United States Patent [19]

Sacks et al.

[11] Patent Number: 4,925,306

[45] Date of Patent: May 15, 1990

[54] ION BOMBARDMENT FURNACE FOR ATOMIC SPECTROSCOPY

[75] Inventors: Richard D. Sacks; Suzanne L. Tanguay, both of Ann Arbor, Mich.

[73] Assignee: The Regents of the University of Michigan, Ann Arbor, Mich.

[21] Appl. No.: 264,137

[22] Filed: Oct. 28, 1988

[51] Int. Cl.⁵ .................. G01J 3/443; G01N 21/67
[52] U.S. Cl. ............................ 356/311; 313/157; 356/314
[58] Field of Search ............... 356/311, 314, 316; 313/153, 157, 158

[56] References Cited

PUBLICATIONS

Trivedi et al., "Magnetically Tailored Arc and Glow Discharge Plasma for Atomic Spectroscopy", Applied Spectroscopy, vol. 41, No. 5, Jul. 1987, pp. 833–843.
"Improved Hollow Cathode Lamps for Atomic Spectroscopy"–Chapters 2 and 6.

Primary Examiner—Vincent P. McGraw
Attorney, Agent, or Firm—Harness, Dickey & Pierce

[57] ABSTRACT

A magnetron glow discharge plasma device is utilized as a furnace for vaporization, atomization and excitation of analytical solution samples of trace elements for atomic emission spectroscopy. The apparatus includes a sample deposited on the glow discharge lamp, a spectrometer optically coupled to the lamp through a transparent wall portion of the furnace, a photoelectric detector connected to the spectrometer for sensing the light and converting the light to an electrical signal and a computer for digitally storing and processing the sent signal.

11 Claims, 2 Drawing Sheets

ION BOMBARDMENT FURNACE FOR ATOMIC SPECTROSCOPY

BACKGROUND AND SUMMARY OF THE INVENTION

This invention relates to a light source for atomic emission spectroscopy and more particularly to a glow discharge device adapted to be used as a furnace for atomic emission spectroscopy.

One technique which exists for vaporizing and atomizing a sample to be analyzed using atomic emission spectroscopy with glow discharge excitation is known as furnace atomic non-thermal excitation spectrometry (FANES). This technique uses resistive heating of a graphite cathode to achieve furnace action to vaporize a sample. This technique requires a large (2.5 Kw) power supply to resistively heat a graphite furnace of the type used in atomic absorption spectroscopy. The large size of the power supply required with this technique inherently makes the FANES device heavy and awkward to use. One of the most difficult problems associated with analytical devices utilizing atomic emission spectroscopy is the separation of the spectral signal due to the analyte from the background light spectra of the ion plasma.

Accordingly, it is an object of the present invention to provide a glow discharge furnace for use in atomic emission spectroscopy using a relatively small power supply making the present invention therefore more economical. It is another object of the present invention to provide an analytical apparatus that is more sensitive to analytes than has previously been attainable.

The preferred embodiments of the present invention include an ion bombardment furnace comprising a magnetron glow discharge lamp having a closed cylindrical chamber containing an ionizable gas and having a center post cathode therein. The lamp in one embodiment is physically located between poles of an electromagnetic so that a magnetic flux field passes through the chamber coaxial with the cathode. In another embodiment, the magnetic field is provided by a tubular stack of ring shaped permanent magnets arranged around the cathode. In both embodiments, the magnetic flux field is directed coaxially with the cathode and a magnetic field of approximately 1.25 kG is typical.

The chamber includes a transparent window in the outer wall for passage of light emitted by excited atoms. The apparatus according to the invention includes focusing mirrors which focus the emitted light and direct this light into a spectrometer which separates the emitted light into a spectrum. A grating or other dispersive element within the spectrometer is then set to pass a narrow bandwidth of wavelengths to a photoelectric detector. The detected light of the selected wavelength is then converted into an electrical signal which is proportional to the intensity of the detected light. The electrical signal is then sent to a display device.

The chamber also has a closable sample access port through which an analyte solution may be inserted and deposited onto the cathode. In addition, the chamber includes a gas inlet and outlet for purging the chamber volume with an ionizable gas such as argon. Positioned concentrically around and spaced from the cathode inside the chamber is a ring shaped anode. The cathode and anode are connected externally to a DC power supply sufficient to cause initial ionization of the argon gas within the chamber initially forming a plasma.

Operation of the ion bombardment furnace for atomic spectroscopy in accordance with the present invention will now be described. An analyte solution is first micropipetted through the access port into the chamber and deposited onto the cathode. The chamber is evacuated and then flushed with argon gas. A pressure of approximately 1 to 5 Torr of argon is then maintained. An electrical current is supplied to the cathode by applying a direct current (DC) potential between the cathode and anode setting up a radial electric field to cause initial ionization of the argon gas and formation of the plasma about the cathode. This DC potential also causes a cathode current to initially heat the cathode.

The presence of the magnetic field retains the electrons formed in the plasma in the proximity of the cathode and enhances the bombardment of neutral atoms of the argon gas. This in turn enhances the production of positive ions. These positive ions then bombard the cathode causing rapid further heating of the cathode and rapid vaporization of the analyte.

The vaporized analyte is excited in the glow discharge plasma. Characteristic light is then emitted by the electrons in the excited atoms as the electrons return to a lower energy state. This light is passed out of the chamber, focused, spectrally separated in the spectrometer, and selectively detected by a photomultiplier tube detector positioned about the exit slit from the spectrometer.

The photomultiplier tube detects light at the selectively passed wavelength and converts this detected light to an electrical signal proportional to the intensity of light emitted. The high signal to noise ratio achievable with this arrangement suggests an absolute limit of trace element detection in the analyte in accordance with this invention in the picogram range.

Other features and advantages of the present invention will become apparent to those skilled in the art to which this invention relates from the subject description of the invention and the appended claims taken in conjunction with the accompanying drawing.

DETAILED DESCRIPTION OF THE INVENTION

Figure 1:
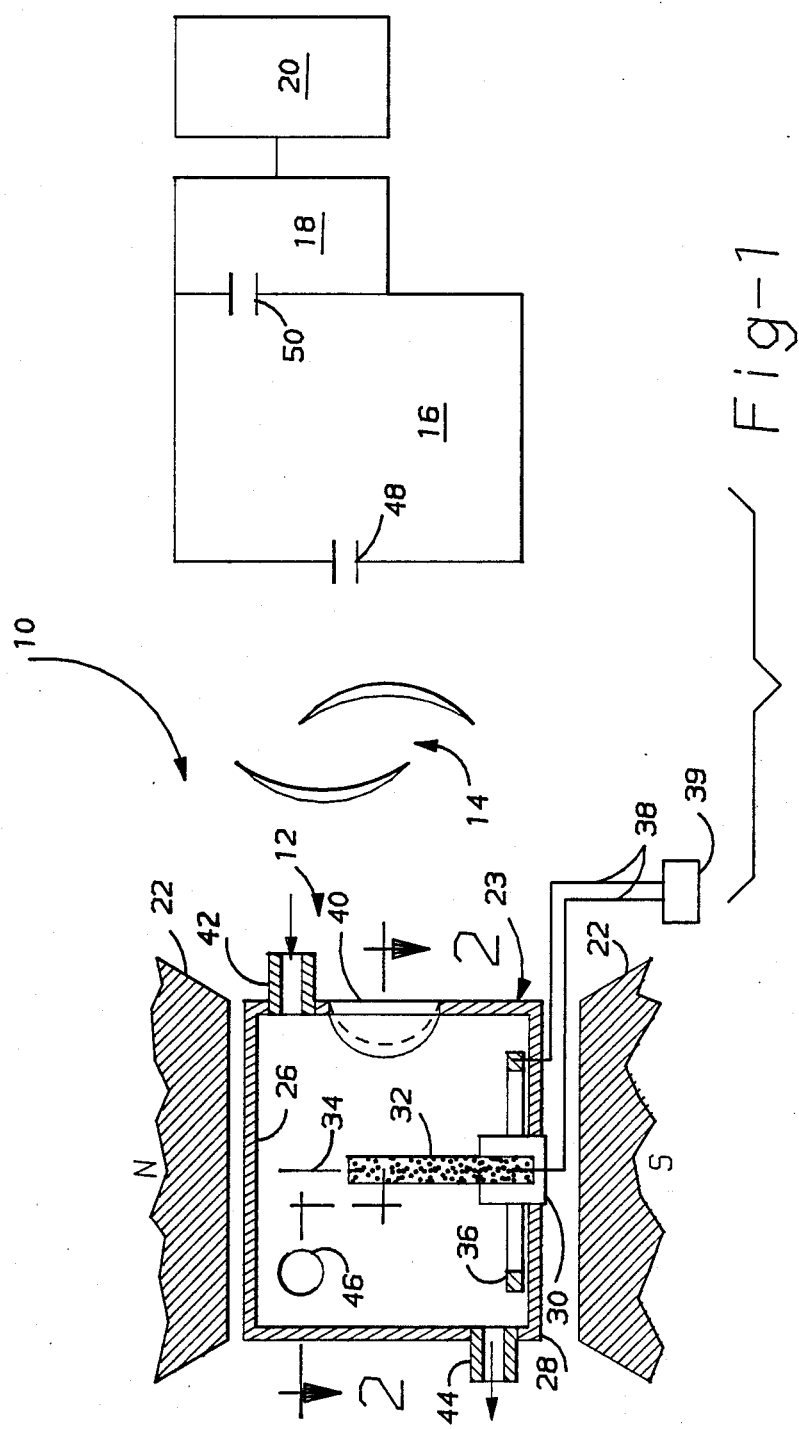
FIG. 1 is a sectional view of one embodiment of the ion bombardment furnace coupled schematically to the remaining portions of the apparatus of the present invention.

The apparatus for detecting the presence of trace elements in a sample by atomic emission spectroscopy according to the present invention is generally indicated at 10 in FIG. 1. The apparatus comprises an ion bombardment furnace 12 coupled optically via optical focusing mirrors 14 to a spectrometer 16. The spectrometer 16 is in turn coupled to a detector 18 which converts the optical signal passed from the spectrometer to an electrical signal which is in turn connected to a storage and display device such as a computer.

The ion bombardment furnace 12 is shown in sectional view in FIG. 1 to illustrate the essential components of the furnace. In the embodiment shown in FIGS. 1 and 2, furnace 12 is positioned in the gap between two pole pieces 22 of an electromagnet. This electromagnet provides a preferably constant magnetic field through furnace 12.

Figure 2:
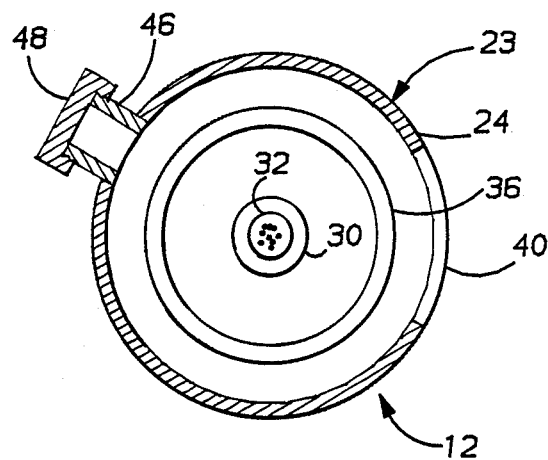
FIG. 2 is a sectional view of the furnace taken along the line 2—2 in FIG. 1.

The ion bombardment furnace 12 is a housing 23 forming a hollow chamber which is used to confine an ionizable gas such as neon or argon. This chamber, as shown in FIGS. 1 and 2, has a tubular wall closed at the ends by end caps 26 and 28. Tubular wall 24 and end caps 26 and 28 may be made of a non-magnetic material such as polycarbonate plastic or a non-magnetic metal such as aluminum. Mounted on end cap 28 is a centrally located ceramic insulator 30 which supports one end of an elongated cathode member 32, preferably of cylindrical shape, made of graphite. The graphite cathode 32 has its central axis 34 aligned coaxially with the magnetic flux field produced between pole pieces 22. The graphite cathode 32 is preferably of cylindrical shape. The exterior may be coated with a pyrolitic material to prevent absorption of the sample into the cathode.

Also fixed within housing 23 is an annular anode 36 supported from end cap 28 and positioned concentrically around cathode 32 and axis 34. The cathode 32 and anode 36 are electrically connected by leads 38 to a direct current power supply 39.

A transparent window 40 is provided in tubular wall 24 which allows emitted light to pass out of furnace 12 as will be subsequently described. Window 40 is preferably made of quartz. Any other spectroscopically transparent, high temperature material may also be used.

A pair of inlet and outlet ports 42 and 44, respectively, are also provided into housing 23. Inlet port 42 is used to inject an ionizable gas such as argon or neon into the housing 23 and a vacuum pump (not shown) is connected to the outlet port 44 so that the entire housing 23 may be purged of air and filled with the ionizable gas and then maintained at a desired pressure during operation of the ion bombardment furnace. This pressure is optimally maintained between 1 and 4 Torr. Also extending through the tubular wall 24 of housing 23 is a closable access port 46 best shown in FIG. 2. Access port 46 includes a cap 48 which is removed to allow insertion of a micropipette for deposition of a sample onto cathode 32 as will be more fully described below.

The ion bombardment furnace in the present invention is basically a magnetron configuration glow discharge lamp. Properties of this type of lamp are described in detail in Tanguay et al., "Radiative And Electrical Properties Of A Center-Post Cathode Magnetron Glow Discharge Device", 42 Applied Spectroscopy 576, (1988), which is incorporated herein by reference.

In the ion bombardment furnace 12, an ionization plasma is produced by application of a direct current via leads 38 from cathode 32 through the ionizable gas to anode 36. This current causes some initial resistive heating of cathode 32. This current also produces a radial electric field between cathode 32 and anode 36.

The presence of the magnetic field between poles 22 passing through housing 23 and crossing the radial electric field between cathode 32 and anode 36 causes a pinching effect on the plasma which tends to hold or trap electrons in closed paths within the plasma volume. By preventing the escape of electrons, the filler gas ionization by hot electrons in the high energy tail of the kinetic energy distribution of the ions is enhanced.

Figure 3:
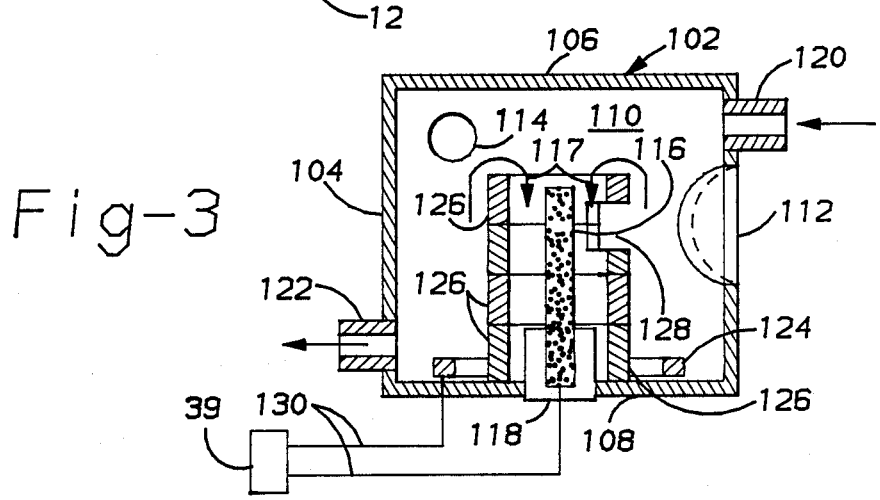
FIG. 3 is a sectional view of an alternative embodiment of the ion bombardment furnace according to the present invention.

In the cylindrical magnetron configuration shown in FIGS. 1 through 3, the electron paths tend to be circles which are concentric with cathode member 32 and anode member 36. The concentration of trapped electrons in the plasma volume increases the probability of neutral argon or other gas atoms undergoing ionizing collisions with these electrons. When high plasma current density to the cathode such as 200 milliamps per square centimeter is achieved by the DC current source, positive ion bombardment of the cathode results in additional heating of the cathode member to temperatures in excess of 2000 degrees Celcius.

At these temperatures, the sample deposited on the surface of the cathode 32 is rapidly vaporized, exciting the atoms of the sample such that light emission takes place as excited electrons in the atom return to a lower energy state. This light emission is chacteristic of the particular atom vaporized. The intensity of the light emitted corresponds to the concentration of the atoms in the vaporized sample. Accordingly, detection and quantitative measurement of the intensity of this light emission is a direct indication of trace element concentration within the sample.

The characteristic light emitted by the vaporized and excited sample passes through window 40 and is directed by optical mirrors 14 through an entrance slit 48 in spectrometer 16. Spectrometer 16 is preferably a Czerny-Turner spectrometer equipped with, for example, a 1200 line/millimeter diffraction grating. The spectrometer 16 is adjusted to pass a narrow bandwidth of wave lengths to the detector 18 through exit slit 50. The detector 18 is basically a photomultiplier tube which in turn converts the light emitted and passed through the exit slit 50 from the spectrometer 16 to an electrical signal which is in turn fed to a display and storage device 20. Alternatively, an array detector may be utilized to sense a broader range of wavelengths from the spectrometer 16. In this manner, simultaneous multi-element analysis may be performed.

The display and storage device 20 may be a digital oscilloscope, a computer, or other electronic storage and display device capable of recording the electrical signal from the detector 18.

The use of positive ion bombardment of the cathode 32 to heat the cathode 32 to the high temperatures required for sample vaporization and operation of the glow discharge lamp permits the use of a much smaller power supply on the order of 200 watts while enhancing the sensitivity over similar instruments currently available.

An alternative preferred embodiment of the ion bombardment furnace for atomic spectroscopy according to the present invention is shown in FIG. 3. The principal difference between the furnace 100 in FIG. 3 and the previously described furnace 12 is that in furnace 100, no external electromagnet is required. The magnetic field parallel to the central axis of the cathode is provided by ring shaped permanent magnets mounted inside furnace 100 concentrically around the cathode forming a tubular magnet as described below.

Ion bombardment furnace 100 comprises a housing 102 having a tubular wall 104 and a pair of end caps 106 and 108 forming a closed chamber 110.

As in the previously described embodiment, housing 102 includes a window 112 made of quartz or other spectroscopically transparent high temperature material in tubular wall 104. A closable sample access port 114 is also provided for entrance and deposition of a sample onto a central elongated cathode 116. Central cathode 116 is a graphite cylindrical post having one end embedded in a ceramic insulating support 118 which is in turn secured to end cap 108.

Housing 102 also includes an inlet port 120 and an outlet port 122. As in the previously described embodiment, inlet 120 is used to inject an ionizable gas such as argon into chamber 110 and exhaust port 122 is connected to a vacuum pump to exhaust unwanted gases from chamber 110.

Positioned concentrically around and spaced from the cathode 116 is an annular anode 124. A stacked arrangement of one or more ring or tubular shaped permanent magnets 126 is positioned between cathode 116 and anode 124. The stacked arrangement of magnets 126 produces a magnetic field which is generally coaxial with cathode 116 near the surface of cathode 116 as indicated by arrows 117.

An aperture 128 is formed through a portion of the stacked arrangement of magnets 126. Aperture 128 is aligned with window 112 so that light emitted from an excited atom adjacent the cathode 116 during operation of the furnace can pass directly through aperture 128 and through window 112 and be focused, detected and processed as described above.

This configuration of magnets within housing 102 permits a much smaller arrangement of the ion bombardment furnace according to the present invention. Either electromagnets or permanent magnets may be used in the internal stacked arrangement of this embodiment. However, use of permanent magnets is preferred because it eliminates the requirement for one power supply. A variety of permanent magnet materials may be utilized in this alternative embodiment. Use of rare earth magnet such as samarium-cobalt or neodymium magnets may be preferred as this allows further miniaturization of the overall furnace assembly. Use of permanent magnets placed in the chamber 110 also reduces the complexity of the overall system and also reduces the total cost.

Operation of the alternative preferred embodiment shown in FIG. 3 is identical to that described above for the first embodiment. A sample is inserted into chamber 110 through access port 114 and deposited onto the surface of the cathode 116. Housing 102 is then closed and argon gas is injected through port 120 and exhausted through port 122 to purge the chamber 110 of extraneous gases. Preferably, a pressure of 1-4 Torr is then maintained in chamber 110.

A DC potential is applied between cathode 116 and anode 124 via electrical leads 130 to initially heat cathode 116 and ionize the fill gas to produce the initial plasma within chamber 110. The presence of the magnetic field from permanent magnets 126 once again holds the electrons within the plasma volume close to cathode 116 thus enhancing the ionization of the fill gas and therefore production of positive ions which in turn bombard the cathode 116 further heating the cathode to vaporize the sample. As the sample is vaporized, light characteristic of the atoms contained in the sample is emitted which passes through aperture 128 and through window 112 for detection and display as described above.

Figure 4:
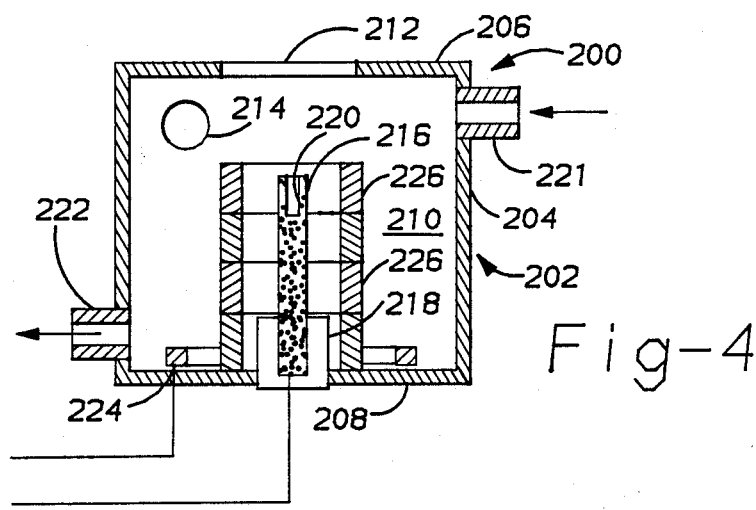
FIG. 4 is a sectional view of a second alternative embodiment of the ion bombardment furnace according to the present invention.

A second alternative preferred embodiment of the ion bombardment furnace for atomic spectroscopy according to the present invention is shown in FIG. 4. This preferred embodiment is similar to that shown in FIG. 3 except that the analyte is deposited in a cavity in the cathode and the transparent window is positioned in the wall opposite the cavity in the cathode. This arrangement prevents radial expansion of the analyte during vaporization which enhances the sensitivity of the detected signal from the analyte. In this embodiment, an additional mirror may be provided outside the window to redirect the vertically emitted light from the furnace. In all other respects, the system remains as described above and shown in FIG. 1.

Ion bombardment furnace 200 comprises a housing 202 having a tubular wall 204 and a pair of end caps 206 and 208 forming a closed chamber 210.

As previously described, housing 202 includes a window 212 made of quartz or other spectroscopically transparent material in end cap 206. A closable sample access port 214 is also provided for entrance and deposition of the sample onto a central elongated graphite cathode 216. Central cathode 216 is a graphite cylindrical post having one end embedded in a ceramic insulating support 218 which is in turn secured to end cap 208. A cavity 220 is bored into the opposite end of cathode 216. The cavity 220 is designed to receive and hold the sample deposited therein during vaporization. The hollow cavity 220 limits radial expansion of the analyte during vaporization which enhances the production of light emission from the trace elements in the analyte. This emitted light is then transmitted through window 212 and then processed as previously described.

Housing 202 also includes an inlet port 221 and an outlet port 222. As in the previously described embodiments, inlet 221 is used to inject an ionizable gas such as argon into chamber 210 and exhaust port 222 is connected to a vacuum pump to exhaust unwanted gases from the chamber 210.

Positioned concentrically around and spaced from cathode 216 is an annular anode 224. A stacked arrangement of one or more ring or tubular shaped permanent magnets 226 is positioned between cathode 216 and anode 224. The stacked arrangement of magnets 226 produces a magnetic field which is coaxial with cathode 216 near the surface of cathode 216 as in the previous embodiments.

As the analyte is vaporized during operation of the furnace, the emitted light is transmitted directly from the end of cathode 216 and therefore an aperture is not required through a portion of the stacked arrangements of magnets 226.

Once again, the configuration of magnets within housing 202 permits a compact arrangement of the ion bombardment furnace according to the present invention. Either electromagnets or permanent magnets may be used in the internal stacked arrangement in this alternative embodiment. As previously discussed, use of permanent magnets is preferable because of the elimination of one power supply.

Operation of the second preferred embodiment shown in FIG. 4 is identical to that described for the first and second embodiments. The additional feature of the cavity in the end of the cathode 216 significantly enhances the production of light emission from the analyte and therefore significantly increases the sensitivity of the instrument.

While the above description constitutes the preferred embodiments of the present invention, it will be appreciated that the invention is susceptible to modification, variation and change without departing from the proper scope and fair meaning of the accompanying claims.

What is claimed is:

1. An apparatus for analyzing a sample by atomic emission spectroscopy comprising:
   a hollow chamber confining an ionizable gas, said chamber having at least one wall, said wall having a transparent portion;
   an elongated cathode member fixed to said chamber and extending into said chamber, said member having a central axis;
   a sample containing at least one trace element;
   a ring shaped anode member mounted in said chamber and concentrically spaced from said cathode member;
   a closable access port through said wall for inserting said sample into said chamber and depositing said sample onto said cathode;
   a spectrometer optically coupled to said transparent portion;
   means for supplying a constant electrical current between said anode and said cathode members establishing an electric field between said cathode and anode members to initially heat said cathode member and to ionize said gas into a plasma of positive ions and electrons, said positive ions bombarding said cathode to further heat said cathode; and
   means for forming a magnetic flux field in said chamber including at least one tubular magnet within said chamber coaxially positioned around said cathode member, said flux field being directed parallel to said axis and crossing said electric field so as to retain said electrons in said plasma whereby said positive ions bombarding said cathode vaporize said sample and cause emission of light from said vaporized sample which passes through said transparent portion to said spectrometer.

2. The apparatus according to claim 1 wherein said/magnet is a permanent magnet.

3. The apparatus according to claim 2 wherein said tubular magnet comprises a plurality of ring shaped permanent magnets stacked coaxially and concentrically around said cathode, at least one of said rings having an aperture therethrough, said aperture being aligned radially with said transparent wall portion for passage of said light from said cathode through said stack of ring shaped magnets and through said transparent wall portion to said spectrometer.

4. The apparatus according to claim 2 wherein said magnet is a rare earth permanent magnet.

5. The apparatus according to claim 1 wherein said cathode has an open cavity therein for receiving said sample and said transparent wall portion is positioned in line with said open cavity.

6. The apparatus according to claim 1 wherein said ionizable gas within said hollow chamber is at a pressure between 1 and 5 Torr.

7. The apparatus according to claim 1 wherein a DC potential is applied to said anode and cathode members to produce said electric field.

8. An apparatus for detecting the presence of trace elements in a sample by atomic emission spectroscopy comprising:
   a magnetron glow discharge lamp having a generally cylindrical cathode member therein and a transparent wall portion, said lamp producing a light from ion bombardment of said cathode, said lamp including a hollow chamber confining an ionizable gas, said cathode member having an elongated shape with one end fixed to said chamber and the other end extending into said chamber, said member having a central axis, a ring shaped anode member mounted in said chamber and concentrically spaced from said cathode member, a closable access port through said wall for inserting said sample into said chamber and depositing said sample onto said cathode, means for supplying a constant electrical current between said anode and said cathode members establishing an electric field between said cathode and anode members to initially heat said cathode member and to ionize said gas into a plasma of positive ions and electrons, said positive ions bombarding said cathode to further heat said cathode, means for forming a magnetic flux field in said chamber including at least one tubular magnet within said chamber coaxially positioned around said cathode member, said flux field being directed parallel to said axis and crossing said electric field so as to retain said electrons in said plasma whereby said positive ions bombarding said cathode vaporize said sample and cause emission of characteristic light from said trace elements in said vaporized sample which passes through said transparent wall portion to said spectrometer;
   a sample deposited on said cathode;
   a spectrometer optically coupled to said lamp through said wall portion, said spectrometer receiving light produced by said lamp;
   a detector connected to said spectrometer for sensing said light and converting said light to an electrical signal; and
   a computer for digitally storing and processing said signal.

9. The apparatus according to claim 8 wherein said cathode member has a hollow open cavity at the other end for receiving said sample, said cavity opening toward said transparent wall portion.

10. The apparatus according to claim 8 wherein said ionizable gas within said hollow chamber is at a pressure between 1 and 5 Torr.

11. The apparatus according to claim 8 wherein a DC potential is applied to said anode and cathode members to produce said electric field.

* * * * *